US008287523B2

United States Patent
Wong et al.

(10) Patent No.: US 8,287,523 B2
(45) Date of Patent: Oct. 16, 2012

(54) SYSTEMS AND METHODS FOR HISTORICAL DISPLAY OF SURGICAL OPERATING PARAMETERS

(75) Inventors: Wayne S. Wong, Irvine, CA (US); Wendy Chao, Irvine, CA (US); Michael J. Claus, Newport Coast, CA (US); Paul Rockley, Corona Del Mar, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 1370 days.

(21) Appl. No.: 11/851,572

(22) Filed: Sep. 7, 2007

(65) Prior Publication Data
US 2008/0064935 A1 Mar. 13, 2008

Related U.S. Application Data

(60) Provisional application No. 60/824,896, filed on Sep. 7, 2006.

(51) Int. Cl.
*A61B 17/00* (2006.01)
(52) U.S. Cl. .............................................. 606/1; 604/22
(58) Field of Classification Search ............... 606/1, 4–6, 606/10–12; 607/88, 89; 604/19–22
See application file for complete search history.

(56) References Cited

U.S. PATENT DOCUMENTS

| 5,454,722 | A | * | 10/1995 | Holland et al. ............... 434/271 |
| 6,397,286 | B1 | | 5/2002 | Chatenever et al. |
| 6,629,948 | B2 | | 10/2003 | Rockley et al. |
| 7,400,752 | B2 | | 7/2008 | Zacharias |
| 2003/0159141 | A1 | * | 8/2003 | Zacharias ....................... 725/37 |
| 2003/0176774 | A1 | | 9/2003 | Hickle et al. |
| 2006/0050144 | A1 | | 3/2006 | Kennedy |
| 2007/0223574 | A1 | | 9/2007 | Roman et al. |
| 2007/0236514 | A1 | | 10/2007 | Agusanto et al. |
| 2007/0238981 | A1 | | 10/2007 | Zhu et al. |

FOREIGN PATENT DOCUMENTS

| EP | 1712210 | 10/2006 |
| WO | 2006/060423 | 6/2006 |

OTHER PUBLICATIONS

International Search Report for Application No. PCT/US2007/077846, mailed on Feb. 29, 2008, 2 pages.

* cited by examiner

*Primary Examiner* — Ahmed Farah
(74) *Attorney, Agent, or Firm* — Abbott Medical Optics Inc.

(57) ABSTRACT

The invention is generally directed to systems and methods for medical care, and more particularly to systems and methods for historical display of surgical operating parameters. A first embodiment is a surgical system that includes a surgical instrument having a plurality of associated surgical parameters, each parameter having a value at each instant during an associate surgical procedure. The system further includes a computer system configured to record the values of each associated surgical parameter at each instant during an associate surgical procedure and display the values of each associated surgical parameter at each instant in a human readable form.

8 Claims, 3 Drawing Sheets

SYSTEMS AND METHODS FOR HISTORICAL DISPLAY OF SURGICAL OPERATING PARAMETERS

RELATED APPLICATIONS

This application claims priority under 35 U.S.C. §119(e) from U.S. Provisional Application No. 60/824,896, filed Sep. 7, 2006, which is incorporated herein by referenced in its entireties.

FIELD OF THE INVENTION

The field of the invention relates to systems and methods for medical care, and more particularly to systems and methods for historical display of surgical operating parameters.

BACKGROUND OF THE INVENTION

Surgical systems, such as phacoemulsification systems for ophthalmic surgery, typically involve a combination of a number of parameters that are each critical to the behavior and performance of that system. These parameters can create complex and dynamic environments. For example, in the case of phacoemulsification, established parameters, such as vacuum, flow, ultrasound power, foot pedal position, and irrigation pressure all interact with one another to influence the safety and efficacy within the chamber of an eye.

In procedures such as these, it would be desirable to have a mechanism for providing a historical analysis of each of these parameters and their interrelationship with one another during and after such procedures.

SUMMARY OF THE INVENTION

The invention is generally directed to systems and methods for medical care, and more particularly to systems and methods for historical display of surgical operating parameters. A first embodiment is a surgical system that includes a surgical instrument having a plurality of associated surgical parameters, each parameter having a value at each instant during an associate surgical procedure. The system further includes a computer system configured to record the values of each associated surgical parameter at each instant during an associate surgical procedure and display the values of each associated surgical parameter at each instant in a human readable form.

In another embodiment, the surgical system is further configured to record a video of the associated surgical procedure and display the video along with the values of each associated surgical parameter at each instant in human readable form.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

In order to better appreciate how the above-recited and other advantages and objects of the inventions are obtained, a more particular description of the embodiments briefly described above will be rendered by reference to specific embodiments thereof which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

DETAILED DESCRIPTION OF THE PREFERRED EMBODIMENTS

Figure 1:
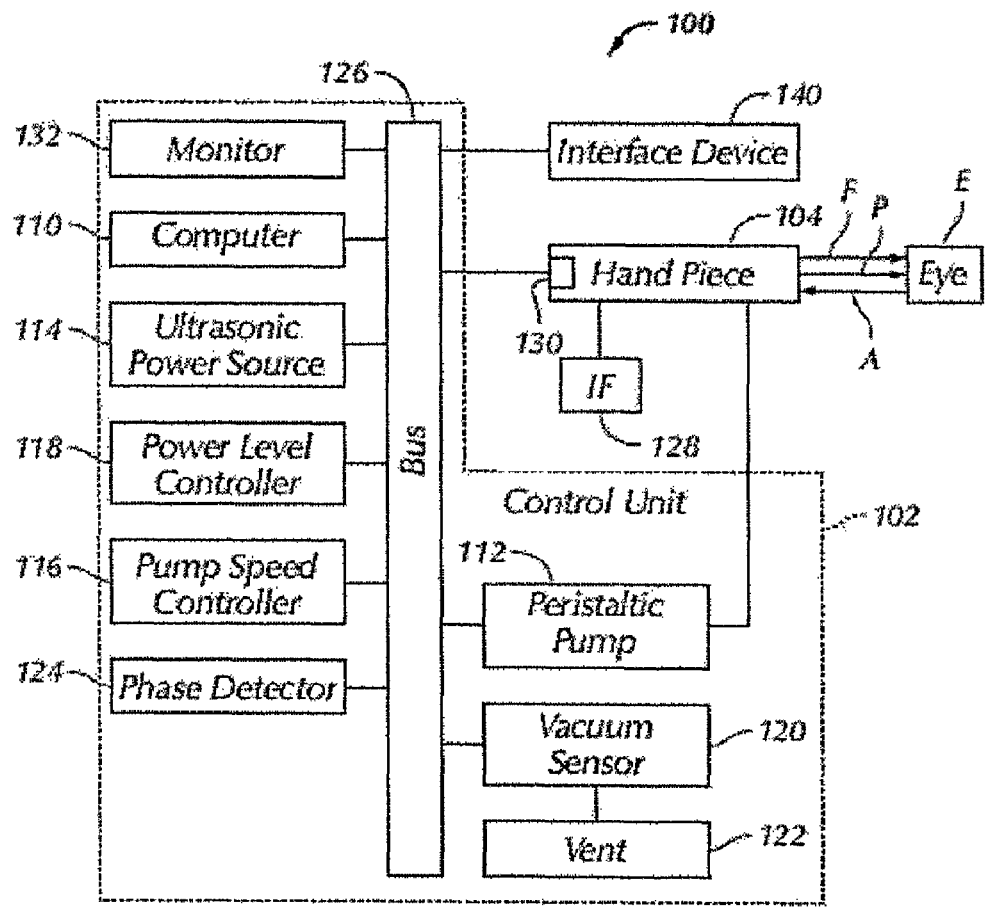
FIG. 1 shows a diagram of a phacoemulsification system known in the art.
Figure 2:
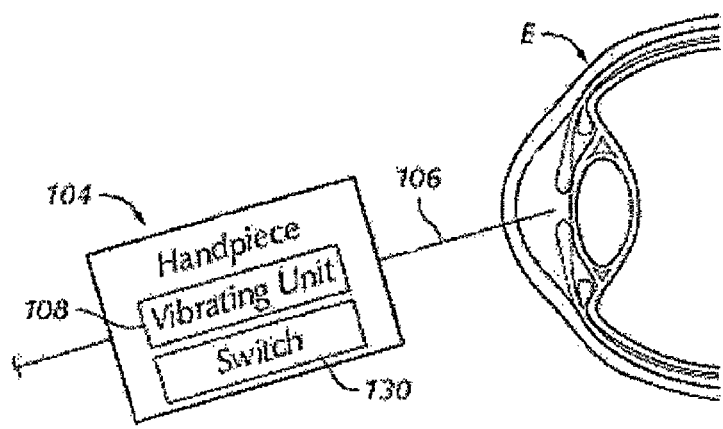
FIG. 2 shows a handpiece for a phacoemulsification system known in the art.

As mentioned above, surgical systems can involve a combination of a number of different parameters that are each critical to the behavior and performance of that system. These parameters can create complex and dynamic environments. An example of such a system is a phacoemulsification system, which removes the lens of an eye damaged by cataract. Parameters associated with a phacoemulsification system include vacuum, flow, ultrasound power, foot pedal position, vitrectomy cut rate, diathermy power, occlusion mode state, pump speed, pump ramp speed, bottle height, infusion pressure, gas infusion pressure, light intensity, and irrigation pressure. Turning to FIG. 1, a functional block diagram of a phacoemulsification system known in the art is shown. The system 100 may include a control unit 102 and a handpiece 104 operably coupled together. As shown in FIG. 2, the handpiece 104 may include a needle 106 for insertion into an eye E and a vibrating unit 108 that is configured to ultrasonically vibrate the needle 106. The vibrating unit 108, which may include, e.g., a piezoelectric crystal, vibrates the needle 106 according to one or more parameters, such as frequency, pulse width, shape, size, duty cycle, amplitude, and so on.

The phacoemulsification system 100 includes a microprocessor computer 110 which is operably connected to and controls the various other elements of the system. In a number of embodiments, the system 100 may include a pump 112, which can be a peristaltic and/or venturi pump known in the art, for providing a vacuum source. In the case of a peristaltic pump, the system may further include a pump speed controller 116. The system further may include a pulsed ultrasonic power source 114 controlled by an ultrasonic power level controller 118. A vacuum sensor 120 provides an input to the computer 110 representing the vacuum level on the output side of the pump 112. Venting may be provided by a vent 122. The system 100 may also include a phase detector 124 for providing an input to the computer 100 that represents a phase shift between a sine wave representation of the voltage applied to the handpiece 104 and the resultant current into the handpiece 104. The functional representation of the system 100 also includes a system bus 126 to enable the various elements to be operably in communication with each other.

In operation, the control unit 102 supplies ultrasonic power to the phacoemulsification handpiece 104. An irrigation fluid source 128 provides irrigation fluid to the handpiece 104. The irrigation fluid and an ultrasonic pulse are applied by the handpiece 104 to a patient's eye E, which are indicated by arrows F and P, respectively. Aspiration of the eye E is achieved by means of the pump 112, which is indicated by arrow A. The handpiece 104 may include a switch 130, which alternatively can be a foot pedal (not shown), for enabling a surgeon to select an amplitude of electrical pulses to the handpiece 104 via the computer 110, the power level controller 118, and the ultrasonic power source 114. The operation of the system 100 in general may be in accordance with the disclosure of U.S. Pat. No. 6,629,948, which is incorporated herein in its entirety by reference.

As shown above, there are many surgical parameters of the system 100. Current systems allow operators to monitor these parameters in real-time during operation; however, as one of ordinary skill in the art will appreciate, operators involved in such procedures may find it desirable to be able to analyze the historical values of these parameters during and/or after such procedures in addition to the real-time values as well their interrelationships.

Figure 3:
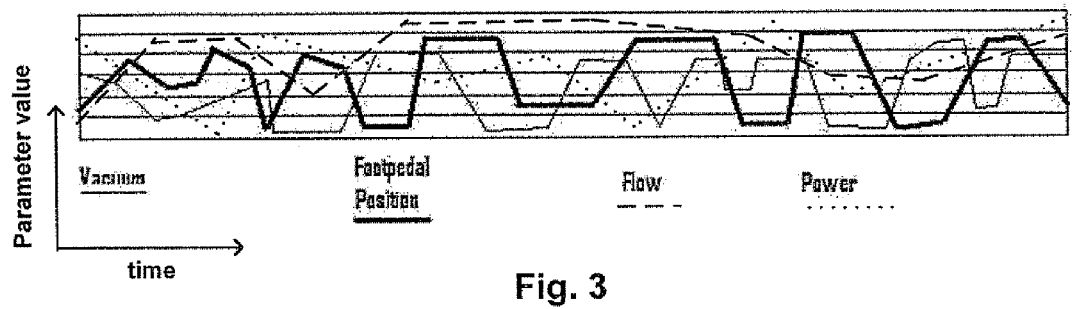
FIG. 3 shows a graphical historical overlay in accordance with a preferred embodiment of the present invention.

Turning to FIG. 3, an approach to providing the historical values for parameters of a surgical system is shown. What is shown in FIG. 3 is a graph of the historical values for four (4) parameters of a phacoemulsification system known in the art, vacuum, foot pedal position, fluid flow rate, and ultrasonic power. The graph shows the historical values for these parameters during a period of time of a surgical procedure. Each parameter can be uniquely color coded and/or have a unique pattern. These parameters can each have their own graph or can preferably share the same x-axis, using different scaling factors for the y-axis, as shown in FIG. 3, so the interrelationship between the parameters is displayed. This approach enables an operator or a witness of the procedure to visualize the changes in the parameters during the procedure, which can be useful for teaching new practitioners the complex nature of the interactions between the parameters. Further, a more complete understanding of a particular instant in a surgical procedure may he gained from evaluating the parameters and system settings at that instant and the parameters and system settings over the previous few seconds and how they have changed leading up to that instant. What is shown in this embodiment is data displayed along a linear graph; however, other formats of display are possible, such as a speedometer type gauge or bar graphs.

Figure 4:
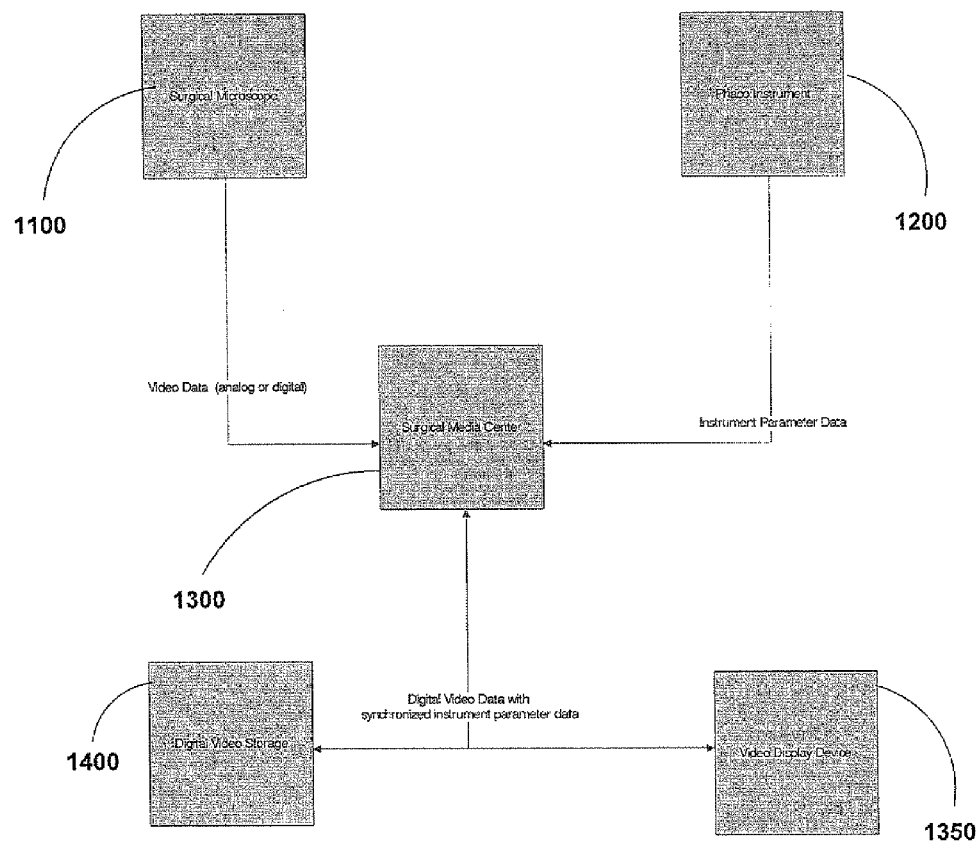
FIG. 4 is a surgical system in accordance with a preferred embodiment of the present invention.

Turning to FIG. 4, a surgical system 1000 that provides the historical values for parameters of a surgical system is shown. The surgical system 1000 includes a surgical instrument, e.g., a phacoemulsification instrument 1200, such as the phacoemulsification system 100 shown in FIG. 1. The surgical system 1000 further includes a surgical microscope 1100 focused on the object of the surgical procedure, e.g., a mammalian eye in the case of a phaco instrument 1200. The surgical microscope 1100, known in the art, also includes video recording capabilities, and the resulting video data (analog or digital) can be transferred to a surgical media center 1300. The surgical media center 1300 is a processing device that manages the multimedia data recorded by the surgical microscope 1100 and that further manages and records surgical parameter data, such as vacuum, power, flow, and foot pedal position in the case of a phaco instrument 1200 during the surgical procedure in real-time.

The surgical system 1000 further includes a digital video storage device 1400 known in the art, coupled with the surgical media center 1300 and configured to store the multimedia data recorded from the surgical microscope 1100. The surgical system 1000 further includes a video display device 1350 coupled to the surgical media center 1300 and the digital video storage device 1400.

In operation, during a surgical procedure associated with the surgical system 1000, the surgical microscope 1100 records a video of the actual procedure, and the surgical instrument 1200 transfers the system settings and surgical parameters, such as those discussed above, to the surgical media center 1300 in real-time during the procedure. The surgical media center 1300, in a preferred embodiment, then synchronizes the temporal relationship between the parameter and settings data from the surgical instrument 1200 and the video data from the surgical microscope 1100. The surgical media center 1300 then can display the video data with a graphical overlay showing the corresponding parameters and system settings at each instant during the procedure and further show historical values in graphical form, such as that shown in FIG. 3, as the values are created in real-time. In the alternative, the graphical overlay can be synchronized with available video data at a later time. This cumulative data, i.e., the video data synchronized with the settings and parameter data can further be archived/stored in the digital video storage device 1400.

In addition, audio data can also be recorded. For example, during the procedure, voice over from the ophthalmologist can be recorded, which can be helpful to new practitioners of the complex nature of the interactions of the parameters. Further, the video and audio data can be edited using multimedia programs known in the art, and such data can be exported to a portable storage device, such as flash memory, compact disc ("CD") or digital video disc ("DVD").

Figure 5:
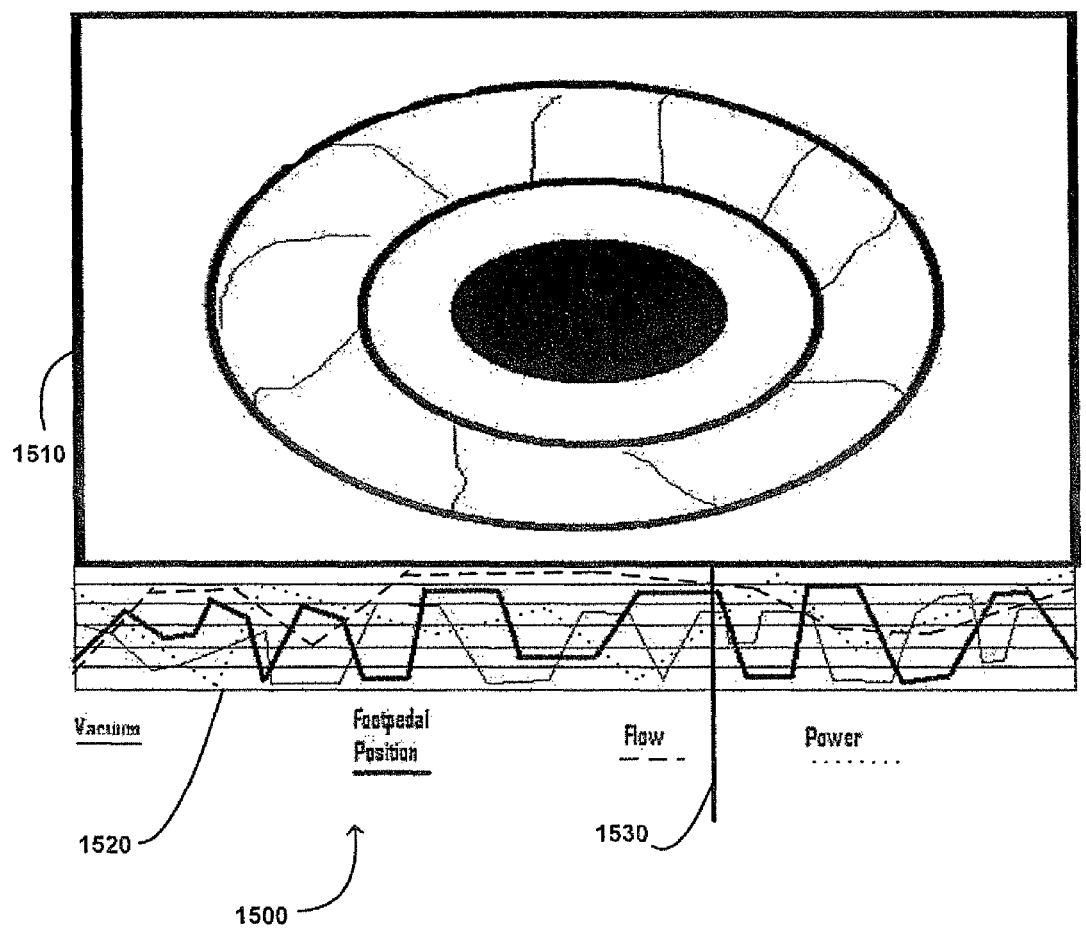
FIG. 5 is a video display in accordance with a preferred embodiment of the present invention.

An example video display 1500 generated by the surgical media center 1300 is shown in FIG. 5. The video display 1500 includes a visual display of the actual procedure 1510, e.g., a phacoemulsification procedure, and further includes a graphical overlay 1520 displaying the historical data for the surgical parameters and system settings such as those described above. Further included is a graphical toolbar 1530 that a user can control to locate a particular instant during the procedure and identify the values of the surgical parameters and system settings during that instant. The toolbar 1530 can be manipulated by the user to slide along the graphical overlay 1520 in any direction. This toolbar 1530 can be used also to advance or rewind the video. At the location of the toolbar 1530 along the graph 1520, a label can be provided displaying the values of the parameters at that location. The users can select which parameters to be displayed on the graph 1520, and the graph 1520 may be displayed in a variety of orientations, e.g., vertically, horizontally, or circularly. Further, the axis can be scaled differently depending on the parameters being displayed, e.g., linearly, logarithmically, exponentially, etc. . . . Moreover, data capture resolution can be varied to provide more or fewer data points for any given time interval. The data rates can also be varied to allow capture and synchronization with high speed video recorders known in the art.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention may appropriately be performed using different or additional process actions, or a different combination or ordering of process actions. For example, this invention is particularly suited for applications involving medical systems, but can be used beyond medical systems in general. As a further example, each feature of one embodiment can be mixed and matched with other features shown in other embodiments. Additionally and obviously, features may be added or subtracted as desired. Accordingly, the invention is not to be restricted except in light of the attached claims and their equivalents.

What is claimed is:

1. A surgical system comprising:
a surgical instrument having a plurality of associated surgical parameters, each parameter having a value at each instant during an associated surgical procedure;
a computer program product that includes a computer-usable medium having a sequence of instructions which, when executed by a processor, causes said processor to execute a process comprising recording the value of each associated surgical parameter at each instant during the associated surgical procedure; and simultaneously displaying the value of each associated surgical parameter at each instant in a human readable form along a single axis.

2. The surgical system of claim 1, wherein the process of the computer program product further comprises recording a video of the associated surgical procedure and displaying the video along with the value of each associated surgical parameter at each instant in human readable form.

3. The surgical system of claim 2, wherein the video and the recorded values are synchronized.

4. The surgical system of claim 1, wherein the associated surgical procedure is a phacoemulsification procedure.

5. The surgical system of claim 2, wherein the process of the computer program product further comprises displaying a graphical toolbar, wherein a user may use the graphical toolbar to select a particular instance during the procedure and identify the values of the surgical parameters during the instance.

6. A surgical system comprising:
a surgical instrument having a plurality of associated surgical parameters, each parameter having a value at each instant during an associated surgical procedure;
a computer program product that includes a computer-usable medium having a sequence of instructions which, when executed by a processor, causes said processor to execute a process comprising recording the value of each associated surgical parameter at each instant during the associated surgical procedure; and simultaneously displaying the value of each associated surgical parameter at each instant in a human readable form, wherein the value is displayed in a speedometer or bar graph form.

7. The surgical system of claim 6, wherein the process of the computer program product further comprises recording a video of the associated surgical procedure and displaying the video along with the value of each associated surgical parameter at each instant in human readable form.

8. The surgical system of claim 7, wherein the process of the computer program product further comprises displaying a graphical toolbar, wherein a user may use the graphical toolbar to select a particular instance during the procedure and identify the values of the surgical parameters during the instance.

* * * * *